United States Patent [19]
Jaeger et al.

[11] Patent Number: 5,306,502
[45] Date of Patent: * Apr. 26, 1994

[54] APPARATUS FOR DELIVERING NITROGLYCERIN TO THE SKIN, PROCESSES FOR THE PRODUCTION THEREOF AND THE USE THEREOF

[75] Inventors: Halvor Jaeger, Neu-Ulm; Hans-Rainer Hoffmann, Neuwied; Reinhold Meconi, Neuwied; Robert-Peter Klein, Neuwied, all of Fed. Rep. of Germany

[73] Assignee: LTS Lohmann Therapie-Systeme GmbH & Co. KG, Neuwied, Fed. Rep. of Germany

[*] Notice: The portion of the term of this patent subsequent to Jun. 30, 2009 has been disclaimed.

[21] Appl. No.: 860,411

[22] Filed: Mar. 30, 1992

Related U.S. Application Data

[63] Continuation of Ser. No. 566,854, Aug. 10, 1990, Pat. No. 5,126,144, which is a continuation of Ser. No. 353,663, Apr. 28, 1989, abandoned.

[30] Foreign Application Priority Data

Sep. 1, 1987 [DE] Fed. Rep. of Germany ....... 3729165
Dec. 23, 1987 [DE] Fed. Rep. of Germany ....... 3743946
Aug. 3, 1988 [WO] PCT Int'l Appl. .................. PCT/DE88/00478

[51] Int. Cl.$^5$ ............................................. A61F 13/00
[52] U.S. Cl. ...................................... 424/443; 424/448
[58] Field of Search ................ 424/448, 449, 465, 443

[56] References Cited

U.S. PATENT DOCUMENTS

| | | | |
|---|---|---|---|
| 4,668,232 | 5/1989 | Cordes et al. | 424/448 |
| 4,797,284 | 1/1989 | Lopes et al. | 424/448 |
| 4,840,796 | 6/1989 | Sweet et al. | 424/448 |
| 5,126,144 | 6/1992 | Jaeger et al. | 424/449 |
| 5,126,144 | 6/1992 | Jaeger et al. | 424/448 |

*Primary Examiner*—Thurman K. Page
*Attorney, Agent, or Firm*—Kalish & Gilster

[57] ABSTRACT

The invention relates to an apparatus for the controlled delivery or release of nitroglycerin to the human or animal skin, preferably in plaster form with a nitroglycerin-impermeable backing layer, a one or multiple-part reservoir containing a pressure sensitive adhesive nitroglycerin in uniform or irregular distribution and optionally a removable protective layer impermeable for nitroglycerin, the reservoir being produced using hot melt pressure sensitive adhesives with a processing temperature of 40° to 80° C., preferably 40° to 60° C. and in particularly preferred manner 40° to 45° C., a process for the production thereof and the use of the apparatus for therapeutic purposes in human and veterinary medicine.

14 Claims, 1 Drawing Sheet

APPARATUS FOR DELIVERING NITROGLYCERIN TO THE SKIN, PROCESSES FOR THE PRODUCTION THEREOF AND THE USE THEREOF

CROSS-REFERENCE TO RELATED APPLICATION

This application is a continuation of application Ser. No. 07/566,854 filed Aug. 10, 1990, now U.S. Pat. No. 5,126,144, which is a continuation of application Ser. No. 07/353,663 filed Apr. 28, 1989, abandoned.

BACKGROUND AND SUMMARY OF THE INVENTION

The invention relates to an apparatus for the controlled delivery or release of nitroglycerin to the human or animal skin, preferably in plaster form, with a backing layer impermeable to the nitroglycerin, a pressure sensitive adhesive one or multiple-part reservoir containing nitroglycerin in uniform or irregular distribution and optionally a removable protective layer impermeable to the nitroglycerin; processes for the production thereof; as well as the use thereof.

Nitroglycerin plasters are already known. The production of nitroglycerin plasters is problematical, in that nitroglycerin is explosive and consequently its evaporation should be avoided.

It is preferable to work at temperatures which are as low as possible, particularly at ambient temperature and frequently the nitroglycerin-containing containing pressure sensitive adhesive layer is produced from the solution. The thus produced, known plaster-like, transdermal, therapeutic systems for the delivery or release of nitroglycerin were able to fulfil the therapeutic requirements, but were complicated and costly to produce.

DE-OS 32 22 800 (ALZA) describes a nitroglycerin plaster, the nitroglycerin-containing matrix being constituted by a nonadhesive, viscous mass obtainable at ambient temperature by thickening a nitroglycerin solution with a rheological agent. U.S. Pat. No. 3,742,951 (CIBA-GEIGY), as well as German Patent 33 15 272 and DE-OS 33 15 245 (LOHMANN/SCHWARZ) describe simply constructed nitroglycerin plasters with pressure sensitive adhesive matrix materials produced from the solution at ambient temperature. It is also known from DE-OS 36 42 931 (CIBA-CEIGY) to use multipart nitroglycerin reservoirs.

The use of solvents in the production of the pressure sensitive adhesive layer is, however, disadvantageous for several reasons. The preparation of the solutions requires at least one further complicated process stage. It involves high technical expenditure and additional costs for handling, whilst for medical purposes extremely pure and therefore expensive solvents must be used for dissolving the adhesive or its starting materials, so as to ensure a corresponding freedom from residue in the transdermal system. Another problem is to ensure freedom from solvents in the plaster and this involves the use of expensive drying sections and suction plants. Additional costs result from the recovery and separation of the solvent, so as to avoid prejudicing the environment. A further risk is constituted by the solvent flammability, particularly in the case of the present explosive active substance. Most organic solvents are also harmful to the human organism, so that complicated protective measures must be taken to protect the working personnel.

The problem of the present invention is therefore to avoid the aforementioned disadvantages of the prior art apparatuses and processes.

According to the invention this problem is solved by an apparatus for delivering nitroglycerin to the skin, in which the nitroglycerin reservoir is produced by using hot melt pressure sensitive adhesive with a processing temperature between 40° and 80° C., preferably 40° and 60° C. and in particularly preferred manner 40° and 55° C.

The nitroglycerin in the hot melt pressure sensitive adhesive can be adsorbed on a carrier, such as lactose, or can be used dissolved in a component of the hot melt pressure sensitive adhesive.

The invention also relates to a process for the production of an inventive apparatus through the continuous or discontinous application of melted hot melt pressure sensitive adhesive containing the nitroglycerin to be released at a hot melt pressure sensitive adhesive temperature between 40° and 80° C., preferably 40° and 60° C. and in particularly preferred manner 45° and 55° C. to a carrier and optional application of the protective layer material.

A further inventive process has the steps of the continuous or discontinuous application of the melted hot melt pressure sensitive adhesive containing the nitroglycerin to be delivered at a hot melt pressure sensitive adhesive temperature between 40° and 80° C., preferably 40° and 60° C. and in particularly preferred manner 40° and 55° C. to a Protective layer material and optional application of a carrier.

Due to the fact that in producing the nitroglycerin reservoir at low temperatures it is possible to operate without solvents, there is a considerable saving on materials, a faster production without time-consuming drying stages and without prejudicing the environment, which inter alia leads to a much less expensive product using a harmless production process.

The term hot melt pressure sensitive adhesive is understood to mean any contact adhesive, which is adequately liquid when hot to permit its problem free application at a temperature above approximately 40° C.

As inventively usable hot melt pressure senstive adhesives can inter alia be used those which are known to the Expert and such as are inter alia described in DE-OS 15 94 268 (SUN OIL C0.), DE-OS 24 13 979 (E.I. DU PONT DE NEMOURS), DE-OS 24 35 863 (DYNAMIT NOBEL AG), DE-OS 28 00 302(CIBA GEIGY), EP-A-104 005 (PERSONAL PRODUCTS CO.), JP 6104 2583 and JP 61 281 810, EP-OS 131 460 (EXXON), EP-OS 234 856 (EXXON). EP-OS 185 992 (EASTMAN KODAK) as well as U.S. Pat. Nos. 3,699,963 and 4,358,557 (EASTMAN KODAK) and express reference is made to this prior art to avoid unnecessary repetition.

The basic polymers can be constituted e.g. by polyamides, polyesters, polycaprolactams, polycaprolactone, ethylene-vinyl acetate copolymers (EVA), ethylene-ethylacrylate copolymers (EEA), polyvinylethers, polyacrylate esters, polyvinylacetals, polyvinylacetates, styrene-butadiene block polymers, isoprene block polymers, polyurethanes, ethylcellulose, cellulose acetate-butyrate, synthetic rubbers (e.g. neoprene rubber), polyisobutylene, butyl rubber, acrylonitrile-butadiene copolymers, epoxy resins, melamine resins, phenol-formaldehyde resins and resorcinol-formaldehyde resins and inter alia the following modifying resins can be used: hydrogenated colophony, polymerized colophony, dimerized resin acids, disproopbrtionated colophony, colophony methyl esters, hydrogenated colophony glycerol esters, hydrogenated colophony methyl esters, pentalesters, hydrogenated colophony triethyleneglycolesters, hydroabiethyl alcohol and its derivatives, glycerol esters ditriolesters and pentaesters of resin acids, polymerized colophony pentalesters, dimerized colophony pentalesters, dimerized colophony glycerol esters, esters of maleic acid or phenol-modified colophony, aromatic and aliphatic hYdrocarbon resins, hydrogenated resins, polyterpene resins, modified terpene resins, waxes, low molecular weight polyethylene and polypropylene and alkyl-styrene copolymers. To these resins can optionally be added plasticizers, such as e.g. adipic acid esters, phosphoric acid esters, phthalic acid esters, polyesters, fatty acid esters, citric acid esters or epoxide plasticizers. It is also possible to admix stabilizers, such as tocopherol, substituted phenols, hydroquinones, pyrocatechols, aromatic amines and optionally also fillers, such as e.g. titanium dioxide, magnesium oxide, zinc oxide and silicon dioxide.

The formation of the components of the apparatus having hot melt pressure sensitive adhesives with a processing temperature between 40° and 80° C. can take place by extrusion, pouring, roller application, knife coating, spraying or a pressing process.

A limit value for the processability of the hot melt pressure senstive adhesive in many of these processes occurs with a viscosity of approximately 80,000 Pa.

If the substrate to be treated with the adhesive, a component of the apparatus, could be damaged by the temperature of the hot-applied adhesive, namely through decomposition, reaction or partial melting, use can be made of a cooled substrate. Cooling can take place by per se known processes, such as by the introduction of cold inert gases or contacting with a cooling surface.

The hot melt pressure senstive adhesive can e.g. be applied in layer form or in individual areas, in accordance with a predetermined pattern, to the protective layer or the covering material.

Typical compositions for hot melt pressure senstive adhesives to be used are those prepared from between 10 and 100% by weight, preferably 20 to 80% by weight and in particularly preferred manner 20 to 50% by weight of polymer, between 10 and 80% by weight, preferably 15 to 60% by weight of plasticizer, between 10 and 80% by weight, preferably 15 to 60% by weight of tackifier, optionally 0.1 to 5% by weight of antiagers and optionally 0 to 70% by weight of fillers, the sum of the percentages of the components always being 100.

Preferably the hot melt pressure sensitive adhesive contains 10 to 50% by weight of styrene-isoprene-styrene synthetic rubber, such as is commercially available under the name CARIFLEX TR 1107 of SHELL, between 10 and 80% by weight of a hydrogenated alcohol, such as is commercially available under the name ABITOL from HERCULES, between 10 and 80% by weight of a hydrocarbon resin, e.g. HERCURES C from HERCULES, between 1 and 40% by weight of esters of vegetable fatty acids, e.g. MICLYOL 812 of DYNAMIT NOBEL and optionally up to 5% by weight of antiagers, such as hydroquinone etc. as well as up to 70% by weight of fillers.

In a further preferred embodiment of the invention the hot melt pressure senstive adhesive has 10 to 50% by weight of a polycaprolactone, e.g. CAPA 650 of INTEROX, between 10 and 80% by weight of a hydrogenated alcohol, e.g. ABITOL of HERCULES, between 10 and 80% by weight of a hydrocarbon resin, e.g. HERCURES C of HERCULES, between 1 and 40% by weight of esters of vegetable fatty acids, such as MIGLYOL 812 of DYNAMIT NOBEL and optionally up to 5% by weight of antiagers, as well as up to 70% by weight of fillers.

It can be advantageous for the hot melt pressure sensitive adhesive to have 10 to 50% by weight of polyethylene-vinyl acetate, such as EVATANE 28-25 of ATOCHEM, between 10 and 80% by weight of a hydrogenated alcohol, e.g. ABITOL of HERCULES, between 10 and 80% by weight of a hydrocarbon resin, e.g. HERCULES C of HERCULES, between 1 and 40% by weight of esters of vegetable fatty acids, e.g. MIGLY0L 812 of DYNAMIT NOBEL and optionally up to 5% by weight of antiagers, such as hydroquinone, etc. and up to 70% by weight of fillers.

A suitable hot melt pressure sensitive adhesive can contain up to 10 to 50% by weight of polyurethane, such as e.g. LUPHEN P 1110 of BASF, between 10 and 80% by weight of a hydrogenated alcohol, e.g. ABITOL of HERCULES, between 10 and 80% by weight of a hydrocarbon resin. e.g. HERCURES C of HERCULES, between 1 and 40% by weight of esters of vegetable fatty acids, e.g. MIGLYOL 812 of DYNAMIT NOBEL and optionally up to 5% by weight of antiagers, as well as up to 70% by weight of fillers.

It is also possible for the hot melt pressure sensitive adhesive to contain up to 10 to 50% by weight of polyamide, such as e.g. EUREL0N 930 of SCHERING, between 10 and 80% by weight of a hydrogenated alcohol, e.g. ABITOL of HERCULES, between 10 and 80% by weight of a hydrocarbon resin, e.g. HERCURES C of HERCULES, between 1 and 40% by weight of esters of vegetable fatty acids, e.g. MIGLYOL 812 of DYNAMIT NBEL and optionally up to 5% by weight of antiagers, as well as up to 70% by weight of fillers.

It is also possible to use a hot melt pressure sensitive adhesive with 10 to 50% by weight of epoxide, e.g. EUREPOX 7001 of SCHERING, between 10 and 80% by weight of a hydrogenated alcohol, e.g. ABITOL of HERCULES, between 10 and 80% by weight of a hydrocarbon resin, e.g. HERCURES C of HERCULES, between 1 and 40% by weight of esters of vegetable fatty acids, e.g. MIGLYOL 812 of DYNAMIT NOBEL and optionally up to 5% by weight of antiagers, such as hydroquinone, etc., as well as up to 70% by weight of fillers.

Another hot melt pressure sensitive adhesive usable in the production of inventive transdermal systems has up to 10 to 50% by weight of polyisobutene with a tacky, rubber-like consistency, such as e.g. OPPANOL B 50 of BASF, between 10 and 80% by weight of a hydrogenated alcohol, e.g. ABTOL of HERCULES, between 10 and 80% by weight of a hydrocarbon resin, e.g. HERCURES C of HERCULES, between 1 and 40% by weight of esters of vegetable fatty acids, e.g. MIGLYOL 812 of DYNAMIT NOBEL and optionally up to 5% by weight of antiagers, as well as up to 70% by weight of fillers.

It is finally preferred to use hot melt pressure sensitive adhesives with a polyester base and which e.g. contain between 10 and 80% by weight of a hydrogenated alcohol. e.g. ABITOL of HERCULES. between 10 and 80% by weight of a hydrocarbon resin, e.g. HERCURES C of HERCULES, between 1 and 40% by weight of esters of vegetable fatty acids, e.g. MIGLYOL 812 of DYNAMIT NOBEL and optionally up to 5% by weight of antiagers, as well as up to 70% by weight of fillers.

Inventive apparatuses can also have one or more nitroglycerin reservoirs, in which the nitroglycerin is present in a concentration higher than the active substance-possessing hot melt pressure sensitive adhesive layer, so that higher nitroglycerin doses can be processed and consequently the apparatus can remain in use longer prior to being replaced. Typical constructions appear in DE-OS 36 29 304 (LOHMANN). Preferred constructions of the invention are given in the subclaims, to which express reference is hereby made.

The production of the melts necessary for producing the inventive apparatus takes place by per se known processes. During the processing of nitroglycerin as an explosive and volatile substance, the following processing measures are advantageous:

A) Working at temperatures which are as low as possible,
B) Raising the external pressure by known measures,
C) Saturation of the vapour chamber over the melt with the vaporous nitroglycerin and working in an encapsulated system and
D) working with the minimum nitroglycerin proportion in the melt.

It is appropriate to work in a closed system, in order to avoid an unregulated evaporation of the nitroglycerin and possibly a collection of explosive quantities thereof on cool regions of the plant, such as e.g. in exhaust systems.

BRIEF DESCRIPTION OF THE DRAWINGS

Further features and advantages of the invention are described hereinafter relative to the drawings, wherein show.

DESCRIPTION OF PREFERRED EMBODIMENTS

Figure 1:
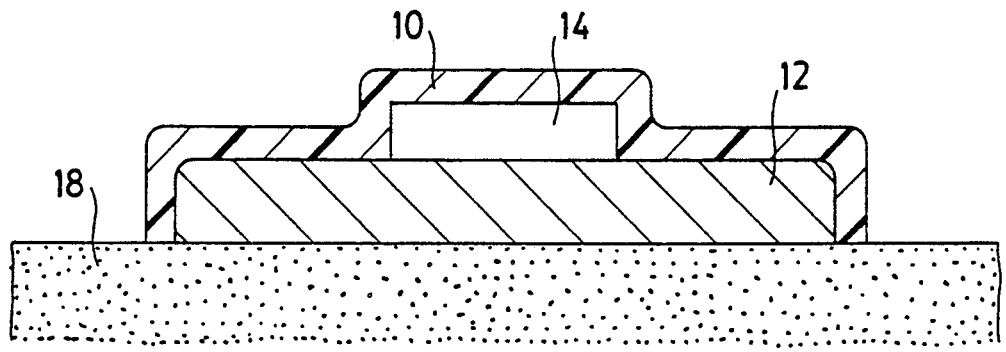
FIG. 1: diagrammatically a section through an inventive apparatus with nitroglycerin depot.

FIG. 1 shows a preferred embodiment of an inventive apparatus as a transdermal system for the delivery of nitroglycerin to the skin. It has a nitroglycerin-permeable hot melt pressure sensitive adhesive 12, a nitroglycerin depot 14, in which the nitroglycerin has a higher concentration than in the hot melt pressure sensitive adhesive 12 and a nitroglycerin-impermeable backing layer 10 on which rests the nitroglycerin depot 14. The apparatus is stuck to the skin 18.

Nitroglycerin now migrates continuously at a predetermined rate through the hot melt pressure sensitive adhesive into the skin 18, so that the nitroglycerin content of the hot melt pressure sensitive adhesive 12 decreases. The reduction of the nitroglycerin quantity is compensated by the after-flow of nitroglycerin from the nitroglycerin depot 14, so that over a predetermined period of time there is a predeterminable equilibrium concentration of the nitroglycerin in the hot melt pressure sensitive adhesive 12, which ensures the delivery of constant nitroglycerin quantities to the skin 18.

Figure 2:
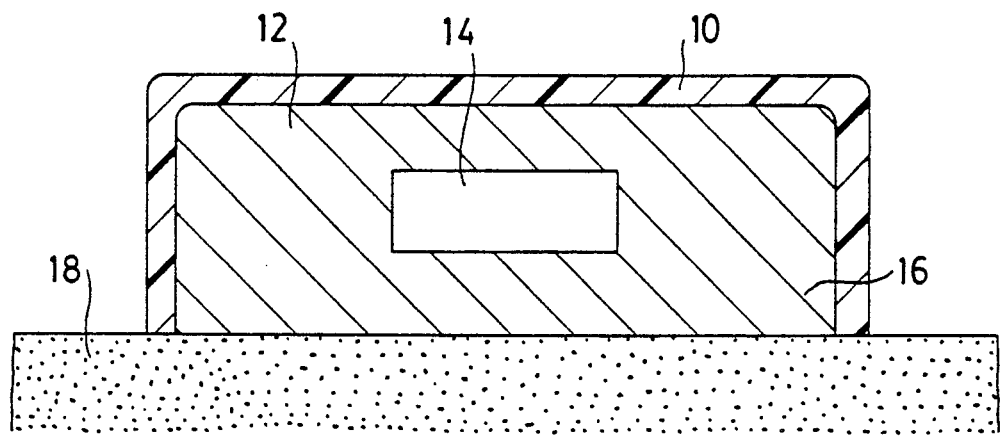
FIG. 2: a diagrammatically represented section through a further inventive apparatus with a nitroglycerin depot.

FIG. 2 shows a further preferred embodiment of an inventive apparatus, in which a nitroglycerin deposit 14 is surrounded on all sides by hot melt pressure sensitive adhesive 12. This embodiment is particularly appropriate if a large contact surface between the nitroglycerin depot and the hot melt pressure sensitive adhesive is desired for the rapid nitroglycerin release to the said adhesive.

Figure 3:
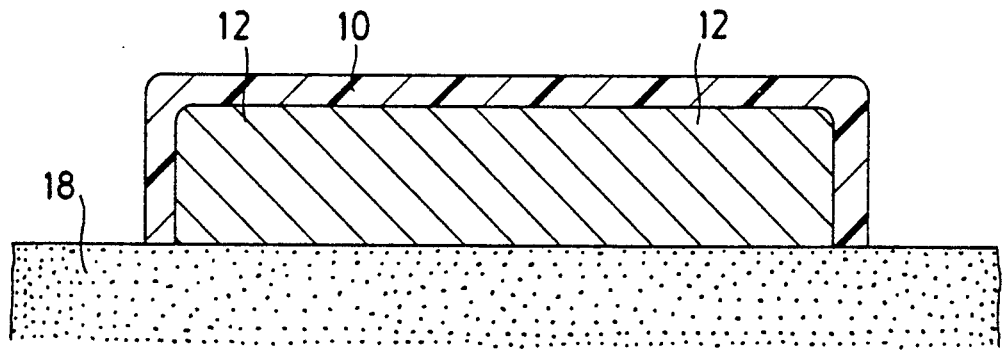
FIG. 3: a diagrammatically represented section through another embodiment of an inventive apparatus without active substance depot.

FIG. 3 shows another simple embodiment of an inventive apparatus, on which a nitroglycerin-containing hot melt pressure sensitive adhesive 12 is applied to a nitroglycerin-impermeable backing material 10 in such a way that the latter covers the adhesive 12 on three sides. By means of the free hot melt pressure sensitive contact adhesive surface, the same is stuck to the skin 18, so that a whole-area contact is ensured over the entire application surface and the transfer of the nitroglycerin from the hot melt pressure sensitive adhesive to the skin always takes place over a constant surface and at a constant speed.

Hereinafter the inventively improved production of a nitroglycerin-containing transdermal system is described. Firstly a mixture of the components of the hot melt pressure sensitive adhesive is prepared with the nitroglycerin. This mixture is brought to the processing temperature and applied from the melt to a backing material. The further processing, such as the application of an adhesively finished protective layer material takes place in the conventional way. The nitroglycerin can be incorporated in adsorbed manner in the hot melt pressure sensitive adhesive both in a solution, preferably dissolved in one of the components of the adhesive, or also on a carrier material, such as lactose.

A particular advantage of the inventive process is that both following the application of the hot melt pressure sensitive adhesive, e.g. by means of a large slot nozzle, the carrier or protective layer material can be lined on, so that through covering the hot melt pressure sensitive adhesive layer evaporation of the nitroglycerin in the freshly prepared system can be suppressed.

The production of a nitroglycerin plaster is described hereinafter:

EXAMPLE 15.58 g of an ethylene-vinylacetate copolymer, such as is commercially available under the name Evatane 28-25 from Atochem are mixed with 20.4 g of hydroabietyl alcohol, such as is commercially available under the name ABITOL from Hercules, 30.4 g of a tackifier based on aliphatic hydrocarbon resins, such as is commercially available under the name Hercures from Hercules, as well as 3.4 g of a plasticizer based on esters of middle-chain vegetable fatty acids (commercially available under the name MIGLYOL 812 from Dynamit Nobel) and melted at a temperature of 110° C. After cooling to 50° to 60° C., to this mixture are added accompanied by stirring 26.6 g of nitroglycerin-lactose triturate (corresponding to 2.7 g of pure nitroglycerin). This mixture is then coated onto a polyester film siliconized and aluminium vapour treated on one side (weight per unit area of adhesive film 402 g/m$^2$) and an aluminized polyester film is applied thereto. The thus obtained laminate was cut into 16 cm$^2$ rectangular plasters and individually packed in sealed bags in per se known manner.

It is obviously also possible to produce inventively other transdermal therapeutic systems containing nitroglycerin and using hot melt pressure sensitive adhesives, so that the aforementioned examples are in no way intended to restrict the protective scope and instead merely illustrate the many possible uses of hot melt pressure sensitive adhesives in this field.

We claim:

1. Process for the production of an apparatus for controlled transdermal release of nitroglycerine to skin, with a pressure sensitive adhesive nitroglycerine-resevoir with a distribution fo the nitroglycerine, said process comprising producing the pressure sensitive adhesive-nitroglycerine producing the pressure sensitive adhesive-nitroglycerine reservoir by using a hot melt pressure sensitive adhesive with a processing temperature of 40° to 80° C., wherein the hot melt adhesive is produced from between 10 to 80% by weight of polymer, between 1 to 80% by weight of plasticiser, and between 10 and 80% by weight of tackifier, whereas the sum of percentages always is 100.

2. Process according to claim 1, wherein the hot melt pressure sensitive adhesive is produced from between 20 to 80% by weight of polymer.

3. Process according to claim 1, wherein the hot melt pressure sensitve adhesive is produced from between 20 to 50% by weight of polymer.

4. Process according to claim 1, wherein the hot melt pressure sensitive adhesive is produced from between 15 to 60% by weight of plasticisers.

5. Process according to claim 1, wherein the hot melt pressure sensitive adhesive is produced from between 15 to 60% by weight of tackifier.

6. Process according to claim 1 and further comprising 0.1 to 5% by weight of anti-agers.

7. Process according to claim 1 and further comprising 0 to 70% by weight of fillers.

8. Process for the production of an apparatus for controlled transdermal release of nitroglycerine to skin, with a pressure sensitive adhesive nitroglycerine-reservoir with a distribution of the nitroglycerine, said process comprising producing the pressure sensitive adhesive-nitroglycerin reservoir by using a hot melt pressure sensitive adhesive with a processing temperature of 40° to 80° C., wherein the hot melt adhesive is produced from between 10 to 80% by weight of polymer, between 1 to 80% by weight of esters acting as plasticiser, and between 10 and 80% by weight of tackifier, whereas the sum of percentages always is 100.

9. Process for the production of an apparatus for controlled trandsermal release of nitroglycerine to skin, with a pressure sensitive adhesive nitroglycerine-reservoir with a distribution of the nitroglycerine, said process comprising producing the pressure sensitive adhesive-nitroglycerine reservoir by using a hot melt pressure sensitive adhesive with a processing temperature of 40° to 80° C., wherein the hot adhesive is produced from between 10 to 80% by weight of polymer, between 1 to 80% by weight of fatty acid esters acting as plasticiser, and between 10 and 80% weight of tackifier, whereas the sum of percentages always is 100.

10. Process according to claim 8 wherein esters of vegetable fatty acids are present as plasticisers.

11. Process for the production of an apparatus for controlled transdermal release of nitroglycerine to skin, with a pressure sensitive adhesive nitroglycerine-reservoir with a distribution of the nitroglycerine, said process comprising producing the pressure sensitive adhesive-nitroglycerine reservoir by using a hot melt pressure sensitive adhesive with a processing temperature of 40° to 80° C., wherein the hot melt adhesive is produced from between 10 to 80% by weight of polymer, between 1 to 40% by weight of esters acting as palsticizer, and between 10 and 80% by weight of tackifier, whereas the sum of percentages always is 100.

12. Process for the production of an apparatus for controlled transdermal release of nitroglycerine to skin, with a pressure sensitive adhesive nitroglycerine-reservoir with a distribution of the nitroglycerine, said process comprising producing the pressure sensitive adhesive-nitroglycerine reservoir by using a hot melt pressure sensitive adhesive with a processing temperature of 40° to 80° C., wherein the hot melt adhesive is produced from between 10 to 50% by weight of polymer selected from the group consisting of styrene-isoprene-styrene, polycaprolactone, polyethylene-vinyl acetate, polyurethane, polyamide, epoxide, polyisobutene and polyester, between 10 to 80% by weight of a hydrogenated alcohol, and between 10 and 80% by weight of a hydrocarbon resin, and between 1 and 40% by weight of esters of vegetable fatty acids, whereas the sum of percentages always is 100.

13. The process of claim 12, wherein the adhesive contains up to 5% by weight of antiagers.

14. The process of claim 12, wherein the adhesive contains up to 70% by weight of fillers.

* * * * *

UNITED STATES PATENT AND TRADEMARK OFFICE
CERTIFICATE OF CORRECTION

PATENT NO. : 5,306,502
DATED : April 26, 1994
INVENTOR(S) : Halvor Jaeger, et al.

It is certified that error appears in the above-identified patent and that said Letters Patent is hereby corrected as shown below:

In the Claims:

Column 7, line 13, replace "fo" with --of--;
        line 15, delete "producing the pressure sensi-";
        line 16, delete "tive adhesive-nitroglycerine"
Column 8, line 10, after the word "hot" insert --melt--;
        line 13, after "80%" insert --by--.

Signed and Sealed this

Eighteenth Day of October, 1994

*Attest:*

BRUCE LEHMAN

*Attesting Officer*      *Commissioner of Patents and Trademarks*